United States Patent
Mendelovici et al.

(10) Patent No.: US 6,809,221 B2
(45) Date of Patent: *Oct. 26, 2004

(54) PROCESS FOR PREPARING (+)-CIS-SERTRALINE

(75) Inventors: Marioara Mendelovici, Rechovot (IL); Tamar Nidam, Yehud (IL); Gideon Pilarsky, Holon (IL); Neomi Gershon, Kfar Saba (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/365,795

(22) Filed: Feb. 12, 2003

(65) Prior Publication Data

US 2003/0166970 A1 Sep. 4, 2003

Related U.S. Application Data

(62) Division of application No. 09/805,829, filed on Mar. 14, 2001, now Pat. No. 6,552,227.
(60) Provisional application No. 60/189,355, filed on Mar. 14, 2000.

(51) Int. Cl.⁷ ............................................. C07C 211/00
(52) U.S. Cl. ...................... 564/308; 564/304; 564/428
(58) Field of Search ................................ 564/308, 304, 564/428

(56) References Cited

U.S. PATENT DOCUMENTS

| | | | |
|---|---|---|---|
| 4,536,518 A | 8/1985 | Welch, Jr. et al. | |
| 5,248,699 A | 9/1993 | Sysko et al. | |
| 5,463,126 A | 10/1995 | Williams | |
| 6,452,054 B2 | 9/2002 | Aronhime et al. | |
| 6,495,721 B1 | 12/2002 | Schwartz et al. | |
| 6,500,987 B1 | 12/2002 | Schwartz et al. | |
| 6,552,227 B2 * | 4/2003 | Mendelovici et al. | ....... 564/308 |
| 6,593,496 B1 | 7/2003 | Quallich | |

FOREIGN PATENT DOCUMENTS

| | | |
|---|---|---|
| WO | WO 98/27050 | 6/1998 |
| WO | WO 99/47486 | 9/1999 |
| WO | WO 99/57093 | 11/1999 |
| WO | WO 01/16089 | 3/2001 |
| WO | WO 01/30742 | 5/2001 |

OTHER PUBLICATIONS

Willard M. Welch et al, Nontricyclic Antidepressant Agaents Serived from cis–trans–1–Amino–4–Aryltetralins, J. Med. Chem, 1984, 27, pp. 1508–1515.

* cited by examiner

Primary Examiner—Samuel Barts
(74) Attorney, Agent, or Firm—Kenyon & Kenyon

(57) ABSTRACT

The present invention is directed to (+)-cis-sertraline hydrochloride and methods of preparation. The present invention also includes processes for making sertraline having a cis/trans ratio greater than 3:1, greater than or equal to 8:1, or between about 8:1 and about 12:1, from the Schiff base of sertralone, sertraline-1-imine.

17 Claims, No Drawings

PROCESS FOR PREPARING (+)-CIS-SERTRALINE

CROSS-REFERENCE TO RELATED INVENTIONS

This application is a division of U.S. patent application Ser. No. 09/805,829, filed Mar. 14, 2001 now U.S. Pat. No. 6,552,227 which claims the benefit under 35 U.S.C. §119(e) of provisional application Ser. No. 60/189,355, filed Mar. 14, 2000, which are incorporated herein by reference.

FIELD OF INVENTION

The present invention relates to the novel process of making and purifying (+)-cis-sertraline.

BACKGROUND OF INVENTION

Sertraline hydrochloride, (1S-cis)-4-(3,4-dichlorophenyl)-1,2,3,4-tetrahydro-N-methyl-1-naphthalenamine hydrochloride, having the formula

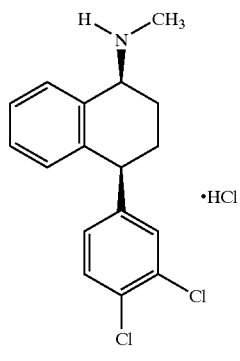

Sertraline hydrochloride is the active ingredient in Zoloft®, a medication approved by the U.S. Food and Drug Administration, for the treatment of depression, obsessive-compulsive disorder and panic disorder.

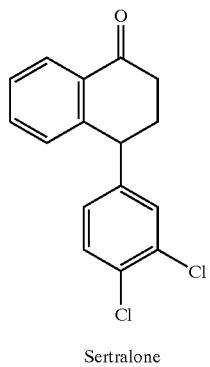

Sertralone

U.S. Pat. No. 4,536,518 describes a synthesis of sertraline hydrochloride from sertralone. The process for synthesizing sertraline hydrochloride from sertralone comprises two steps. First, sertralone is condensed with methyl amine in the presence of an acid catalyst, to yield the Schiff base of sertralone, sertraline-1-imine.

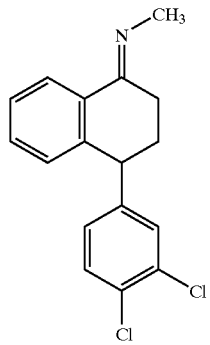

Sertraline 1-imine

The imine, or Schiff base, is then reduced to sertraline. The reduction process of U.S. Pat. No. 4,536,518 comprises the hydrogenation of sertraline-1-imine concentrate at room temperature for two hours over 10% Pd/C catalyst in an atmosphere of hydrogen (1 atm pressure). The product is a racemic mixture of the cis and trans diastereomers ("(±)-cis/trans-sertraline") in the ratio of approximately 3 to 1. This hydrogenation step can introduce a number of contaminants, including dechlorinated side-products, if not carefully controlled. One very problematic group of side products are dechlorinated-sertraline derivatives. It is desirable to have a hydrogenation method that reduces the amount of dechlorinated-sertraline side products or eliminates these side products.

The purification of cis-sertraline from (±)-cis/trans-sertraline as described in the '518 patent is relatively complicated and expensive requiring multiple recrystallizations, and the (±)-cis/trans-sertraline so produced has a cis/trans ratios lower than 3:1. It is therefore desirable to have a method of initially making cis/trans-sertraline base from sertraline-1-imine with cis/trans ratios greater than 3:1. It is also desirable to have a simple and cost effective purification of (+)-cis-sertraline from (±)-cis/trans-sertraline base or from (±)-cis/trans-sertraline hydrochloride.

SUMMARY OF THE INVENTION

The present invention relates to a process for making (±)-sertraline having a cis/trans ratio of greater than about 3:1 comprising the step of hydrogenating sertraline-1-imine at a temperature of at least about 40° C. using a catalyst selected from the group consisting of palladium and platinum. By the processes of the present invention, catalysts include palladium on carbon, palladium on graphite, palladium on carbon paste, and $PtO_2$.

The present invention also relates to a process for making (±)-sertraline with a cis/trans ratio between about 8:1 and about 12:1 comprising the step of hydrogenating sertraline-1-imine at a temperature of at least about 40° C. using a palladium catalyst. By the processes of present invention, suitable catalysts include, palladium on carbon, palladium on graphite, and palladium on carbon paste.

The present invention also relates to a process for making (+)-cis-sertraline hydrochloride comprising the step of reacting an optically active selective precipitant with (±)-sertraline base having a cis/trans ratio of greater than 3:1.

The present invention also relates to a process for making (+)-cis-sertraline which is substantially free of dechlorinated side products, comprising the step of catalytically hydrogenating sertraline-1-amine using $PtO_2$ as a catalyst.

The present invention also relates to a process for making (+)-cis-sertraline hydrochloride from (±)-sertraline hydrochloride with a cis/trans ratio of greater than 3:1 comprising the steps of: generating (±)-sertraline by addition of an aqueous base to (±)-sertraline hydrochloride with a cis/trans ratio of greater than 3:1; resolving the (±)-sertraline so generated; and isolating (+)-cis-sertraline hydrochloride.

The present invention also relates to a process for making (+)-cis-sertraline hydrochloride from (±)-sertraline hydrochloride comprising the steps of: generating (±)-sertraline by addition of a solid base to (±)-sertraline hydrochloride; resolving the (±)-sertraline so generated; and isolating (+)-cis-sertraline hydrochloride.

The present invention also relates to a process for making (+)-cis-sertraline from (±)-sertraline base wherein the (±)-sertraline base has a content of dechlorinated-sertraline side products that is very low, e.g., less than about 1%, or alternatively, wherein the content of dechlorinated-sertraline side products is undetectable by conventional methods, comprising the steps of: generating (±)-sertraline by addition of a solid base to (±)-sertraline hydrochloride; resolving the (±)-sertraline so generated; and isolating (±)-cis-sertraline hydrochloride.

DETAILED DESCRIPTION OF THE INVENTION

The present invention provides a new process for making (±)-cis/trans-sertraline having a cis/trans ratio greater than about 3:1 by hydrogenation of sertraline-1-imine. It also provides new processes for making sertraline from the Schiff base of sertralone, sertraline-1-imine. The methods provided by the present invention provide high cis/trans ratios of (±)-cis/trans-sertraline. Methods of the present invention are also expected to have fewer impurities and side products than prior art methods. Hydrogenation methods of the present invention also have very low amounts of dechlorinated-sertraline side products.

According to the present invention sertraline is prepared from the Schiff base of sertralone, sertraline-1-imine. The sertraline-1-imine may be made by the process of U.S. Pat. No. 4,536,518, the contents of which are incorporated by reference. The sertraline-1-imine is dissolved in an organic solvent such as t-butyl-methyl ether (MTBE), tetrahydrofuran (THF), toluene, ethanol, isopropanol, n-butanol, ethyl acetate, acetone, methanol, or mixtures thereof, and catalytically hydrogenated in the presence of hydrogen gas with warming. Suitable catalysts include platinum and palladium. In a preferred embodiment of the present invention the catalyst is palladium. Preferably the palladium catalyst is palladium on carbon, palladium on graphite or palladium on carbon paste wherein the metal loading of palladium is about 5 to 10% by dry weight. More preferably, the catalyst is 10% Pd/C by weight. In another preferred embodiment of the present invention the catalyst is platinum. More preferably the platinum catalyst is $PtO_2$.

By the methods of the present invention, the reaction is warmed to at least about 40° C. The reaction may be warmed on a heating mantel. Preferably the reaction is warmed to and maintained at about 40° C. to about 80° C. More preferably, the reaction is warmed to and maintained at about 40° C. to about 60° C.

When the reaction is complete, the reaction mixture is filtered, the solvent is removed and the (±)-cis/trans-sertraline isolated. The isolated (±)-cis/trans-sertraline of the present invention has a very low amount of dechlorinated-sertraline side products. Herein, dechlorinated-sertraline side products refers to sertraline derivatives wherein one or both of the 3,4-phenyl chlorine atoms are replaced by hydrogen. In methods of the present invention where palladium is used as the catalyst, the (±)-cis/trans-sertraline isolated has a cis/trans ratio of approximately 8:1 to approximately 12:1, which is a substantial improvement over the cis/trans ratio of about 3:1 reported in the related art. In an embodiment of the present invention where the hydrogenation of sertraline-1-amine uses palladium on graphite as the catalyst in ethanol at about 40° C., the (±)-cis/trans-sertraline isolated has a cis/trans ratio of approximately 12:1. In an embodiment of the present invention where palladium on graphite is used as the catalyst, ethanol is a preferred solvent. In an embodiment of the present invention where palladium on charcoal is used as the catalyst, preferred solvents are t-butyl-methyl ether and toluene. In an embodiment of the present invention wherein the hydrogenation of sertraline-1-amine uses palladium as the catalyst in t-butyl-methyl ether at about 40° C., the content of dechlorinated-sertraline side products is less than about 1%.

By the methods of the present invention where $PtO_2$ is used as the catalyst, no dechlorinated-sertraline side products can be detected, by conventional methods, in the isolated (±)-cis/trans-sertraline by conventional methods. Preferably, the isolated (±)-cis/trans-sertraline is substantially free of dechlorinated-sertraline side products. The (±)-cis/trans-sertraline isolated has a cis/trans ratio of greater than about 3 to 1. Preferably the cis/trans ratio is about 4 to 1. Table 1 provides additional data and reaction conditions concerning the hydrogenation of sertraline-1-imine.

Where the present invention provides methods for preparing (+)-cis-sertraline hydrochloride from crude (±)-cis/trans-sertraline base, the (±)-cis/trans-sertraline base is dissolved in an appropriate organic solvent such as toluene, isopropanol, ethanol, t-butyl-methyl ether, methanol, n-butanol, or ethyl acetate, and the solution is warmed to a temperature such as about 50° C. Resolution of he (±)-cis/trans-sertraline base is facilitated by the use of an optically active selective precipitant. An optically active selective precipitant, such as (D)-mandelic acid, (L)-mandelic acid, (+)-10-camphorsulfonic acid or (−)-10-camphorsulfonic acid, is added to the reaction mixture and the mixture is then heated to reflux. (D)-Mandelic acid and (L)-mandelic acid are preferred; (D)-mandelic acid is more preferred. The mixture is cooled to room temperature and stirred, preferably about 2 hours, or until the reaction is complete. Completion of the reaction may be monitored by methods known in the art. Filtration of the reaction mixture, followed by drying yields the crude (+)-sertraline-precipitant, preferably the crude (+)-sertraline-mandelate. This crude (+)-sertraline-precipitant is. further purified by recrystallization in an appropriate organic solvent. Ethanol and isopropanol are preferred. Ethanol is more preferred.

The recrystallized (+)-sertraline-precipitant is dissolved in an appropriate organic solvent such as toluene, ethyl acetate, isopropanol, t-butyl-methyl ether or hexane. The sertraline-precipitant solution is washed with an aqueous basic solution, such as, 10% sodium hydroxide (NaOH) solution, 10% potassium hydroxide (KOH) solution, and the like, to remove the selective precipitant, e.g., mandelic acid. The organic phase of the solution is further washed with water and the (+)-sertraline base is isolated by solvent evaporation. The (+)-sertraline base is dissolved in an appropriate organic solvent, such as, ethanol, and the solution is cooled. The cooled organic solution is then acidified with hydrochloric acid, while maintaining the reaction temperature at approximately 10° C., to facilitate the formation of (+)-cis-sertraline hydrochloride. The reaction mixture is then stirred at room temperature for an appropriate amount of time, such as, about 2 hours, to facilitate the precipitation of (+)-cis-sertraline hydrochloride. Completion of the reaction may be monitored by conventional methods. The (+)-cis-sertraline hydrochloride Form V is isolated by filtration and drying.

Sertraline hydrochloride Form V is disclosed in U.S. Pat. No. 5,248,699 ("the '699 patent"), the contents of which are incorporated herein by reference. The '699 patent characterizes sertraline hydrochloride Form V by single crystal x-ray analysis, powder x-ray diffraction, infra-red spectroscopy, and different scanning calorimetry. The sertraline hydrochloride Form V that results from practicing the invention as exemplified herein can be characterized by its powder X-ray diffraction pattern. The principal peaks observed are at about 5.2±0.2, 10.4±0.2, 11.0±0.2, 14.3±0.2, 16.5±0.2, 17.3±±0.2, 18.4±0.2, 19.1±0.2, 19.7±0.2, 20.9±0.2, 22.0±0.2, 23.2±0.2, 23.6±0.2, 25.5±0.2, 26.0±0.2, and 29.1±0.2 degrees 2 theta. The IR spectrum of sertraline hydrochloride Form V produced by the present process is characterized by the following bands: 773 $cm^{-1}$, 822 $cm^{-1}$, 1012 $cm^{-1}$, 1032 $cm^{-1}$, 1054 $cm^{-1}$, $1133^{-1}$, $1328^{-1}$, $1562^{-1}$, and 1590 $cm^{-1}$.

The methods of the present invention for making (+)-cis-sertraline allow sertraline-precipitant, or sertraline-mandelate, to be made directly from the sertraline racemate resulting from the hydrogenation, reduction, of the sertraline-1-imine. This improved, efficient and cost effective purification is possible when the sertraline racemate has a relatively high cis/trans ratio, such as, about 8:1 to about 12:1, as well as when the content of dechlorinated-sertraline side products is low, such as, less than about 1%. The methods of the present invention successfully eliminate the need for several purification steps prior to selectively precipitating (+)-cis-sertraline with an optically active selective precipitant.

The present invention also provides an alternative method of making (+)-cis-sertraline hydrochloride. Crude (±)-cis/trans-sertraline having a cis/trans ratio of greater than 3:1 may be treated with hydrochloric acid to make crude (±)-cis/trans-sertraline hydrochloride having a cis/trans ratio of greater than 3:1. The crude (±)-cis/trans-sertraline hydrochloride having a cis/trans ratio of greater than 3:1 is dissolved in an at least partially non-water soluble organic solvent, such as ethyl acetate, isopropanol, t-butyl-methyl ether, n-butanol, iso-butanol, and toluene, or a non-basic water miscible solvent, such as, isopropanol, and washed with an appropriate aqueous basic solution, such as, 10% sodium hydroxide solution, 10% potassium hydroxide solution, and the like, to facilitate the formation of (±)-cis/trans-sertraline base. The organic and aqueous phases are then separated. The resolution of the (±)-cis-sertraline base is facilitated by the use of an optically active selective precipitant. The optically active selective precipitant, as described above, e.g., (D)-mandelic acid, is added directly to the organic phase which contains the (±)-cis/trans-sertraline. The crude (+)-sertraline-precipitant is then crystallized directly from this organic solution. Thus, the present process eliminates the need to recrystallize the sertraline hydrochloride racemate before adding the selective precipitant, such as, (D)-mandelic acid. The (+)-cis-sertraline hydrochloride is then made from the crystallized crude (+)-sertraline precipitate as described above. For example, recrystallized (+)-sertraline-precipitant is dissolved in an appropriate organic solvent such as toluene, ethyl acetate, isopropanol, t-butyl-methyl ether or hexane. The sertraline-precipitant solution is washed with an aqueous basic solution, such as, 10% sodium hydroxide (NaOH) solution, 10% potassium hydroxide (KOH) solution, and the like, to remove the selective precipitant, e.g., mandelic acid. The organic phase of the solution is further washed with water and the (+)-sertraline base is isolated by solvent evaporation. The (+)-sertraline base is dissolved in an appropriate organic solvent, such as, ethanol, and the solution is cooled. The cooled organic solution is then acidified with hydrochloric acid, while maintaining the reaction-temperature at approximately 10° C., to facilitate the formation of (+)-cis-sertraline hydrochloride. The reaction mixture is then stirred at room temperature for an appropriate amount of time, such as, about 2 hours, to facilitate the precipitation of (+)-cis-sertraline hydrochloride. Completion of the reaction may be monitored by conventional methods. The (+)-cis-sertraline hydrochloride Form V is isolated by filtration and drying.

(±)-cis/trans-Sertraline hydrochloride may also be recrystallized once and dissolved in an appropriate organic solvent, such as ethanol, isopropanol, methanol, n-butanol, and iso-butanol. Ethanol is preferred. The optical resolution is performed by adding solid base, e.g., potassium hydroxide, sodium hydroxide, sodium carbonate ($Na_2CO_3$) and sodium bicarbonate ($NaHCO_3$), directly to the sertraline hydrochloride racemate solution. The salts are then removed by an appropriate method, e.g., by filtration. The optically active, selective precipitant, as described above, e.g., (D)-mandelic acid, is added to the organic solution and the (+)-cis-sertraline-precipitant, e.g.,(+)-cis-sertraline-mandelate, is precipitated directly from this organic solution. The resulting crude (+)-cis-sertraline-precipitant is recrystallized. The recrystallized (+)-cis-sertraline-precipitant, e.g.,(+)-cis-sertraline-mandelate, is dissolved in organic solvent and the mandelic acid is removed with base, such as, by washing the organic solution with aqueous basic solutions, e.g., 10–20% sodium hydroxide (NaOH) solution, or 10–20% potassium (KOH) solution. The (+)-cis-sertraline free base is isolated, dissolved in an appropriate organic solvent, and is treated with hydrochloric acid. (+)-cis-Sertraline hydrochloride is precipitated as crystals and dried to give (+)-cis-sertraline hydrochloride Form V.

The methods of the present invention provide a quick, efficient method for accomplishing the very sensitive process of optical resolution. Table 3 provides additional data and reaction conditions concerning optical resolution. The present improved, efficient and cost effective purification is possible when the sertraline racemate has a relatively high cis/trans ratio, such as, about 8:1 to 12:1. The methods of the present invention successfully eliminate the need for several purification steps prior to selectively precipitating (+)-cis-sertraline with an optically active selective precipitant.

The following examples are given for the purpose of illustrating the present invention, and are not intended to limit the invention in any way.

EXAMPLES

Example 1

Step 1: Preparation of Sertraline-1-Imine (Schiff Base)

Sertralone (100 g) was dissolved in toluene (1400 mL) and the solution so obtained was cooled to 0–5° C. Methyl amine gas (38.7 g) was bubbled through the solution while maintaining the temperature between 0–5° C. To the above solution, $TiCl_4$ (20 mL) was added dropwise while maintaining the temperature below 10° C. The reaction mixture was allowed to warm to room temperature and then was stirred at room temperature for 3 hours. Upon completion of the reaction, TiO$_2$ was removed by filtration and the filtrate was evaporated to dryness. The solid obtained after evaporation was sertraline-1-imine (101.17 g; yield 100%).

Step 2: Preparation of (±)-Cis/Trans-Sertraline (Sertraline Racemate) Free Base

A slurry of sertraline-1-imine (Schiff base) (10 g) in t-butyl-methyl-ether (MTBE) (270 mL) was hydrogenated in the presence of Pd/C (10% loading) at 40° C., at 1 atm H$_2$ pressure. After approximately 5 hours the reaction was complete. Filtration of the reaction mixture through a cellite pad and evaporation of the solvent afforded (±)-cis/trans-sertraline free base (sertraline racemate free base) (10 g) as an oil.

TABLE 1

Hydrogenation of sertraline-1-imine

| Solvent | Catalyst | Metal loading | Temperature | Ratio cis/trans racemate |
| --- | --- | --- | --- | --- |
| MTBE | Pd/C | 10% | 40° C. | 9:1 |
| Toluene | Pd/C | 10% | 60° C. | 8:1 |
| EtOH | Pd/graphite | 5% | 40° C. | 12:1 |
| MTBE | Pd/C, paste | 10% | 40° C. | 9:1 |
| MTBE | PtO$_2$ | — | 40° C. | >3:1 |

Step 3: Preparation of Crude (+)-Sertraline Mandelate

Sertraline racemate free base (75.6 g) was dissolved in ethanol (760 mL) and the solution heated to about 50° C. (D)-Mandelic acid (37.6 g) was added and the solution was heated to reflux. The mixture was cooled to room temperature and stirred for 3 hours. Filtration and washing with ethanol followed by drying at about 60° C. afforded the product crude (+)-sertraline mandelate, in 83.7% yield:(40.7 g), 94.6% SS-sertraline, 3.01% RR-sertraline.

The optical purity of the (+)-sertraline mandelate was established by chiral HPLC.

Step 4: Preparation of (+)-Sertraline Mandelate Crystals

Crude (+)-sertraline mandelate (40 g) was crystallized from ethanol (920 mL). The hot solution was treated with active carbon, filtrated and cooled to room temperature. The obtained solid was isolated by filtration and washed with ethanol. After drying, the (+)-sertraline-mandelate crystals are obtained in 82.8 % yield (31.95 g) 99.0% SS-sertraline by area, no RR-sertraline was detected.

Step 5: Preparation of (+)-Sertraline Hydrochloride Form V

The crude (+)-sertraline mandelate crystals in toluene were partitioned between a 10% aqueous solution of NaOH and toluene. The organic solution was washed with water and the solvent was evaporated to dryness to give (+)-sertraline base (6.9 g). The solution of (+)-sertraline base (3.7 g) in ethanol (18.5 mL) was acidified with hydrogen chloride gas while keeping the temperature at about 10° C. Then the mixture was cooled to room temperature and stirred for 2 hours. After filtration, washing of the solid with ethanol and drying, (+)-sertraline hydrogen chloride ((+)-sertraline HCl) Form V was obtained (3.16 g, yield 82.7%), 99.6% SS-sertraline by area, no RR-sertraline was detected.

The procedure of steps 3–5 was performed 5 times as described above. Table 2 includes the specific conditions and results of these 5 experiments.

TABLE 2

| Entry | Sample type | Preparation Conditions | Yield (%) |
| --- | --- | --- | --- |
| 1 | (±) Sertraline base | H$_2$/PtO$_2$ | 61.9 |
|   | (+) Mandelate crude | Toluene, 60° C., room temperature (r.t.), 2 h | 41.7 |
|   | (+) Mandelate crude | Ethanol (EtOH), reflux, r.t. 2 h | 85.5 |
|   | (+) Sertraline · HCl | EtOH/HCl (g) | 83.1 |
|   |   | Overall -yield | 18.3 |
| 2 | (±) Sertraline base | H$_2$/Pd/C | 81.2 |
|   | (+) Mandelate crude | Toluene, 10 vol., 60° C., r.t., 2 h | 45.2 |
|   | (+) Mandelate crystallization I | EtOH, reflux, r.t. 2 h | 86.2 |
|   | (+) Mandelate crystallization II | EtOH abs., reflux, r.t. 2 h | 87.2 |
|   | (+) Sertraline · HCl | EtOH abs./HCl (g) | ~90 |
|   |   | Overall-yield | 24.9 |
| 3 | (±) Sertraline base | H$_2$/Pd/C, MTBE, 40 | 87.7 |
|   | (+) Mandelate crude | Toluene, 10 vol., 60° C., r.t., 2 h | 41.2 |
|   | (+) Mandelate crystallization | EtOH abs., reflux, r.t. 2 h | 88.2 |
|   | (+) Sertraline · HCl |   | ~90 |
|   |   | Overall-yield | 28.75 |
| 4 | (±) Sertraline base | H$_2$/Pd/C | 83 |
|   | (+) Mandelate crude | Toluene, 10 vol., 60° C., r.t., 2 h | 40 |
|   | (+) Mandelate crystallization | EtOH abs., reflux, r.t. 2 h | 86.7 |
|   | (+) Sertraline · HCl | EtOH abs./HCl (g) | 71.7 |
|   |   | Overall-yield | 20.6 |
| 5 | (±) Sertraline base | H$_2$/Pd/C, Toluene, 60° C. | 78 |
|   | (+) Mandelate crude | Toluene, 10 vol., 60° C., r.t., 2 h | 44.2 |
|   | (+) Mandelate crystallization | EtOH abs., reflux, r.t. 2 h | 87.5 |
|   | (+) Sertraline · HCl | EtOH abs./HCl (g) | 80.1 |
|   |   | Overall-yield | 24.2 |

Example 2

Optical Resolution (±)-Sertraline hydrochloride (5 g) was dissolved in ethanol (20 mL) and KOH powder (85%) was added to the solution. The slurry was stirred at room temperature for 2.5 hrs. After stirring the solids were removed by filtration and the solution was treated with D-(−)-mandelic acid (2.66 g). Precipitation occurred and the stirring was continued for 24 hours. (+)-Sertraline-mandelate was isolated by filtration and washed with ethanol and then dried to yield 2.70 g of (+)-sertraline-mandelate.

Optical purity of (+)-sertraline-mandelate was established by chiral HPLC methods. Table 3 provides additional data and reaction conditions concerning the optical resolution of sertraline. In Table 3, the % Enantiomer RR is the percent area of the RR-enantiomer as determined by chiral HPLC; Chiracel OD-H, 250×4.6 nm, 5 μ, column temperature 5° C. In Table 3, the Yield % is the yield of optical resolution, based on the % SS-enantiomer of sertraline hydrochloride practically obtained against the theoretical SS-sertraline hydrochloride enantiomer that could be obtained. The yield was calculated based on the optical purity of (±)-sertraline hydrochloride obtained. In Table 3, the Assay % is the percent of SS-sertraline hydrochloride as determined by chiral HPLC method using SS-sertraline hydrochloride as the standard.

TABLE 3

Optical Resolution

| Entry | Solvent | Base | % Enantiomer RR | Yield (%) | Assay (%) |
|---|---|---|---|---|---|
| 1 | 1-Propanol | 20% aq. NaOH | 2.4 | 83.4 | 99 |
| 2 | n-Butanol | 20% aq. NaOH | 2.7 | 81.9 | 96.1 |
| 4 | Ethyl-acetate | 20% aq. NaOH | 1.06 | 76.9 | |
| 5 | Toluene | 20% aq. NaOH | 2.2 | 75.8 | |
| 6 | t-Butyl-methyl-ether | 20% aq. NaOH | 22.9 | 85.1 | |
| 7 | Ethanol | KOH powder, 85% | 4.6 | 79.3 | 89.3 |

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. A process for making (+)-cis-sertraline hydrochloride from (±)-sertraline base comprising the steps of:
   (a) hydrogenating sertraline-1-imine at a temperature of at least about 40° C. using a catalyst selected from the group consisting of palladium and platinum to obtain (±)-sertraline base having a cis/trans ratio of greater than about 3:1;
   (b) reacting an optically active selective precipitant with (±)-sertraline base to form a (+)-cis-sertraline-precipitant;
   (c) reacting the (+)-sertraline-precipitant with a basic solution to facilitate the formation of the (+)-sertraline base;
   (d) reacting the (+)-sertraline base with hydrochloric acid to facilitate the precipitation of (+)-cis-sertraline hydrochloride; and
   (e) isolating (+)-cis-sertraline hydrochloride.

2. The process of claim 1, wherein the content of dechlorinated-sertraline side products is less than about 1%.

3. The process of claim 1, wherein the cis/trans ratio is between about 8:1 and about 12:1.

4. The process of claim 1 wherein the process of step (b) is carried out in an organic solvent selected from the group consisting of toluene, iso-propanol, ethanol, t-butyl-methyl ether, methanol, n-butanol or ethyl acetate.

5. The process of claim 1 wherein the basic solution is selected from the group consisting of sodium hydroxide aqueous solution and potassium hydroxide aqueous solution.

6. A process for making (+)-cis-sertraline hydrochloride comprising the steps of:
   (a) hydrogenating sertraline-1-imine at a temperature of at least about 40° C. using a catalyst selected from the group consisting of palladium and platinum to obtain (±)-sertraline base having a cis/trans ratio of greater than about 3:1;
   (b) converting the (±)-sertraline base to (±)-sertraline hydrochloride;
   (c) generating (±)-sertraline base by addition of an aqueous base to (±)-sertraline hydrochloride;
   (d) resolving the (±)-sertraline base so generated to form (+)-sertraline base;
   (e) reacting the (+)-sertraline base with hydrochloric acid to facilitate the precipitation of (+)-cis-sertraline hydrochloride; and
   (f) isolating (+)-cis-sertraline hydrochloride.

7. The process of claim 6 wherein step (d) further comprises the steps of:
   (a) reacting an optically active selective precipitant with the (±)-sertraline base; and
   (b) reacting the (+)-sertraline-precipitant with a basic solution to facilitate the formation of (+)-sertraline base.

8. The process of claim 6 wherein the content of dechlorinated-sertraline side products is less than about 1%.

9. The process of claim 6, wherein (±) sertraline hydrochloride is dissolved in a substantially non-water miscible organic solvent.

10. The process of claim 9, wherein the organic solvent is selected from the group consisting of ethyl acetate, isopropanol, n-butanol, t-butyl-methyl ether and toluene.

11. The process of claim 6 wherein the aqueous base is selected from the group consisting of sodium hydroxide solution and potassium hydroxide solution.

12. A process for making (+)-cis-sertraline hydrochloride from (±)-sertraline hydrochloride comprising the steps of:
   (a) hydrogenating sertraline-1-imine at a temperature of at least about 40° C. using a catalyst selected from the group consisting of palladium and platinum to obtain (±)-sertraline base having a cis/trans ratio of greater than about 3:1;

(b) converting the (±)-sertraline base to (±)-sertraline hydrochloride;

(c) generating (±)-sertraline base by addition of a solid base to (±)-sertraline hydrochloride;

(d) resolving the (±)-sertraline base so generated to form (+)-sertraline base;

(e) reacting the (+)-sertraline base with hydrochloric acid to facilitate the precipitation of (+)-cis-sertraline hydrochloride; and (f) isolating (+)-cis-sertraline hydrochloride.

13. The process of claim 12 wherein step (d) further comprises the steps of:

(a) reacting an optically active selective precipitant with the (±)-sertraline base wherein the (±)-sertraline base has a cis/trans ratio of greater than about 3:1 to form a (+)-cis-sertraline-precipitant;

(b) reacting the (+)-sertraline-precipitant with a basic solution to facilitate the formation of (+)-sertraline base.

14. The process of claim 12 wherein the content of dechlorinated-sertraline side products is less than about 1%.

15. The process of claim 12 wherein (±)-sertraline hydrochloride is dissolved in an organic solvent.

16. The process of claim 15, wherein the organic solvent is selected from the group consisting of ethanol, isopropanol, methanol, n-butanol, and iso-butanol.

17. The process of claim 12 wherein the solid base is selected from the group consisting of sodium hydroxide, potassium hydroxide, sodium carbonate and sodium bicarbonate.

* * * * *